US010501658B2

(12) United States Patent
Gouda et al.

(10) Patent No.: US 10,501,658 B2
(45) Date of Patent: Dec. 10, 2019

(54) BIRD-REPELLENT COATING MATERIAL

(71) Applicant: WINTON OSAKA CO., LTD., Osaka-shi, Osaka (JP)

(72) Inventors: Hiroshi Gouda, Nara (JP); Katsumi Funahara, Kurashiki (JP)

(73) Assignee: WINTON OSAKA CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 16/308,581

(22) PCT Filed: Dec. 20, 2017

(86) PCT No.: PCT/JP2017/045670
§ 371 (c)(1),
(2) Date: Dec. 10, 2018

(87) PCT Pub. No.: WO2018/117142
PCT Pub. Date: Jun. 28, 2018

(65) Prior Publication Data
US 2019/0153261 A1 May 23, 2019

(30) Foreign Application Priority Data

Dec. 21, 2016 (JP) .................. 2016-257950

(51) Int. Cl.
| C09D 183/04 | (2006.01) |
| C09D 7/61 | (2018.01) |
| C09D 7/63 | (2018.01) |
| C09D 7/40 | (2018.01) |
| C09D 5/00 | (2006.01) |
| A01N 25/04 | (2006.01) |
| A01N 31/00 | (2006.01) |
| C09D 1/00 | (2006.01) |
| C09D 201/00 | (2006.01) |
| C09D 7/62 | (2018.01) |
| C08K 9/10 | (2006.01) |
| C08K 11/00 | (2006.01) |
| C08K 3/36 | (2006.01) |
| C08K 5/00 | (2006.01) |

(52) U.S. Cl.
CPC .......... *C09D 183/04* (2013.01); *A01N 25/04* (2013.01); *A01N 31/00* (2013.01); *C08K 9/10* (2013.01); *C09D 1/00* (2013.01); *C09D 5/00* (2013.01); *C09D 7/40* (2018.01); *C09D 7/61* (2018.01); *C09D 7/62* (2018.01); *C09D 7/63* (2018.01); *C09D 7/70* (2018.01); *C09D 201/00* (2013.01); *C08K 3/36* (2013.01); *C08K 5/0041* (2013.01); *C08K 11/00* (2013.01)

(58) Field of Classification Search
CPC .......... C09D 183/04; C09D 7/61; C09D 7/63; C09D 7/70; C09D 5/00; C09D 5/0041; C08K 11/00; C08K 3/36
See application file for complete search history.

(56) References Cited

U.S. PATENT DOCUMENTS

| 5,196,451 A | 3/1993 | Greig-Smith et al. |
| 5,846,554 A | 12/1998 | Scher et al. |
| 5,993,842 A | 11/1999 | Scher et al. |
| 6,015,571 A | 1/2000 | Scher et al. |
| 6,077,522 A | 6/2000 | Scher et al. |
| 6,149,843 A | 11/2000 | Scher et al. |
| 7,345,157 B2 | 3/2008 | Miyawaki et al. |
| 7,547,528 B2 | 6/2009 | Miyawaki et al. |
| 7,892,791 B2 | 2/2011 | Miyawaki et al. |
| 7,981,637 B2 | 7/2011 | Miyawaki et al. |
| 8,999,362 B2 | 4/2015 | Delaveau et al. |

FOREIGN PATENT DOCUMENTS

| CN | 105284797 A | 2/2016 |
| JP | H02113836 A | 4/1990 |
| JP | H02502643 A | 8/1990 |
| JP | H0578219 A | 3/1993 |
| JP | H05139910 A | 6/1993 |

(Continued)

OTHER PUBLICATIONS

JP2005143349 English Machine Translation, prepared Mar. 31, 2019. (Year: 2019).*
JP2003047432 English Machine Translation, prepared Mar. 31, 2019. (Year: 2019).*
JPH1112105A Englsh Machine Translation, prepared Mar. 31, 2019. (Year: 2019).*
CN105284797 English Machine Translation prepared Jul. 9, 2019. (Year: 2019).*
International Search Report (English and Japanese) and Written Opinion issued in PCT/JP2017/045670 dated Feb. 6, 2018.
Office Action issued in corresponding Japanese Patent Application No. 2016-257950 dated Dec. 5, 2017, with English translation.
Decision to Grant issued in corresponding Japanese Patent Application No. 2016-257950 dated May 8, 2018, with English translation.

(Continued)

*Primary Examiner* — Christopher M Rodd
(74) *Attorney, Agent, or Firm* — Hamre, Schumann, Mueller & Larson, P.C.

(57) ABSTRACT

Various measures have conventionally been adopted against bird damage, but as yet none has proved decisive. There is moreover no technology that affords sustained repellency of coating materials against bird damage. A bird-repellent coating material according to the present invention contains at least one component selected from the group consisting of a microencapsulated aqueous dispersion of a visual repellent against birds, a microencapsulated volatile olfactory repellent against birds and a powder of a visual repellent against birds, and an aqueous resin vehicle that contains the above component. No bird-repellent coating material has been conventionally produced in which the components and so forth of the material are established taking into consideration the diversity and learning ability of birds. The formulation of the bird-repellent coating material according to the present invention, by contrast, has been devised taking into account the senses of sight and smell in birds.

9 Claims, 3 Drawing Sheets

(56) References Cited

FOREIGN PATENT DOCUMENTS

| | | | |
|---|---|---|---|
| JP | H06219906 A | | 8/1994 |
| JP | H0776502 A | | 3/1995 |
| JP | H07173005 A | | 7/1995 |
| JP | H0886025 A | | 4/1996 |
| JP | H09301803 A | | 11/1997 |
| JP | H1112105 A | | 1/1999 |
| JP | H1119520 A | | 1/1999 |
| JP | H11112105 A | * | 1/1999 |
| JP | H11504030 A | | 4/1999 |
| JP | H11226422 A | | 8/1999 |
| JP | H11256076 A | | 9/1999 |
| JP | H11335205 A | | 12/1999 |
| JP | 2000256104 A | | 9/2000 |
| JP | 2000290104 A | | 10/2000 |
| JP | 2001064102 A | | 3/2001 |
| JP | 2001181109 A | | 7/2001 |
| JP | 2002039051 A | | 2/2002 |
| JP | 2002173401 A | | 6/2002 |
| JP | 2003047432 A | * | 2/2003 |
| JP | 2003238309 A | | 8/2003 |
| JP | 2004188325 A | | 7/2004 |
| JP | 2005133282 A | | 5/2005 |
| JP | 2005143349 A | | 6/2005 |
| JP | 2005323590 A | | 11/2005 |
| JP | 2005330380 A | | 12/2005 |
| JP | 2008260742 A | | 10/2008 |
| JP | 3155554 U | | 11/2009 |
| JP | 2010035558 A | | 2/2010 |
| JP | 2010202570 A | | 9/2010 |
| JP | 2012044885 A | | 3/2012 |
| JP | 2014162757 A | | 9/2014 |
| JP | 2014180251 A | | 9/2014 |
| JP | 2015074651 A | | 4/2015 |
| WO | 2013112989 A1 | | 8/2013 |

OTHER PUBLICATIONS

Shi et al., "Airport Bird Strike Prevention Series", by Hefei University of Technology Press, Oct. 2014, with machine translation; 7 pages provided.

Shi et al., "Architectural Coatings and Coating Technology 400 Questions", by Chemical Industry Press, Beijing, first printed in Mar. 1996, with machine translation; 6 pages provided.

Office Action issued in corresponding Chinese Patent Application No. 201780027256.3 dated Apr. 17, 2019; with English abstract of the Chinese application; 7 pages provided.

Zesen, et al., "Waterborne architectural coating production technology", Paint and Coating Practical Technology Series, Chinese Traditional Publishing House, 2007, 8 pages with translation.

2nd Office Action issued in corresponding Chinese Patent Application No. 201780027256.3, dated Oct. 12, 2019, 16 pages with translation, JP 2005-323590 being previously submitted.

* cited by examiner

[Fig. 1]
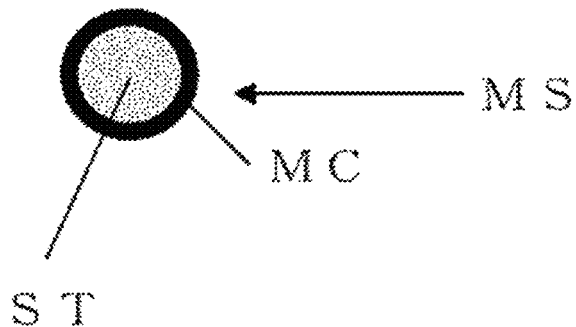
[Fig. 2]
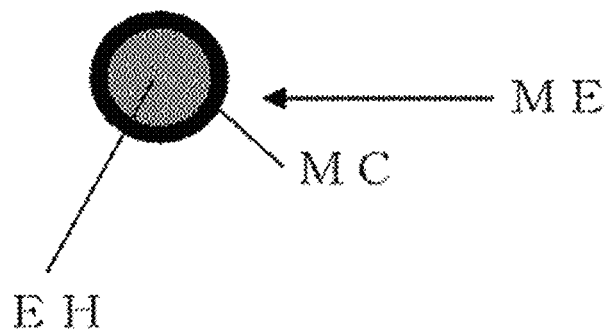
[Fig. 3]
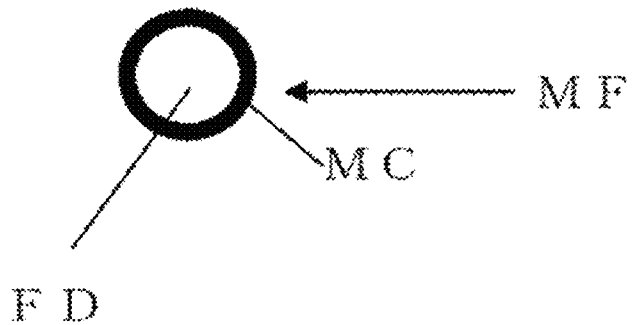

[Fig. 4]
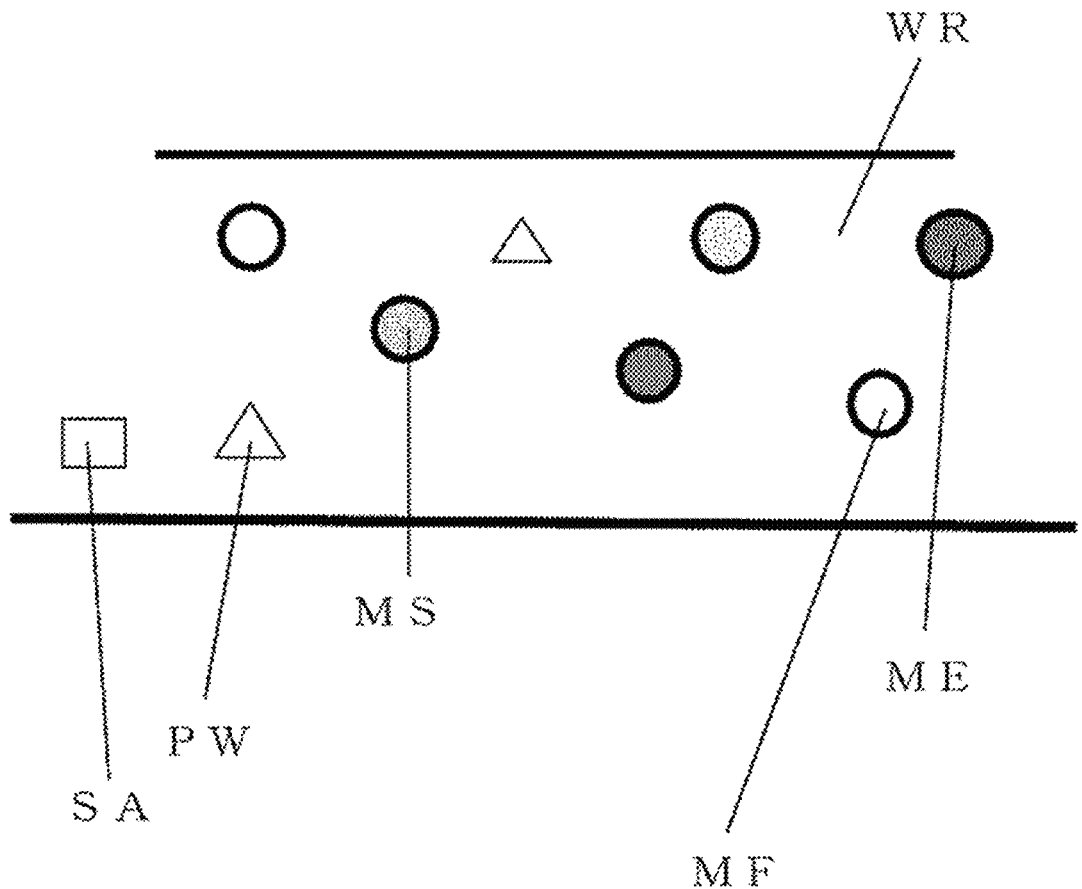
[Fig. 5]
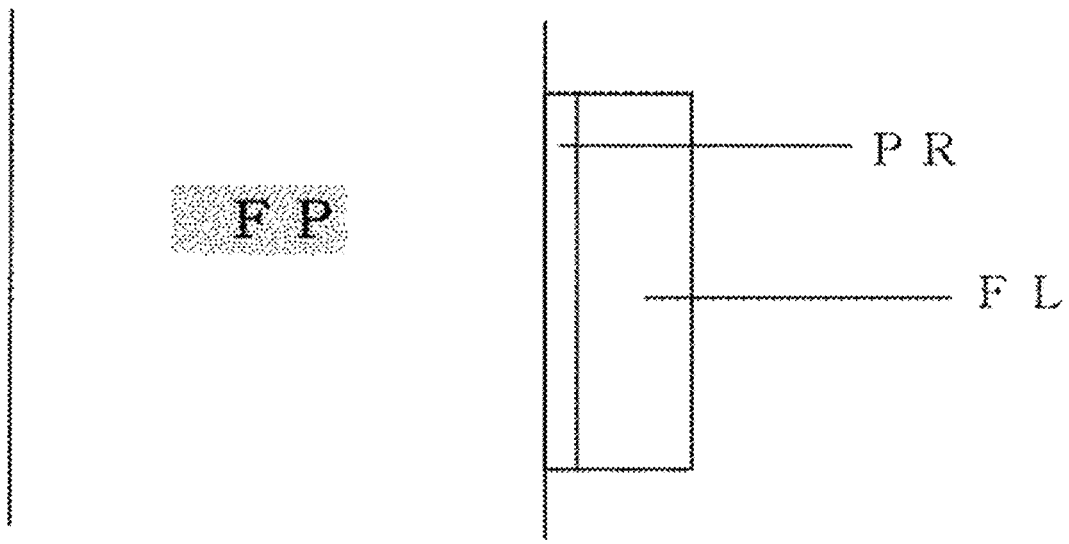

[Fig. 6]
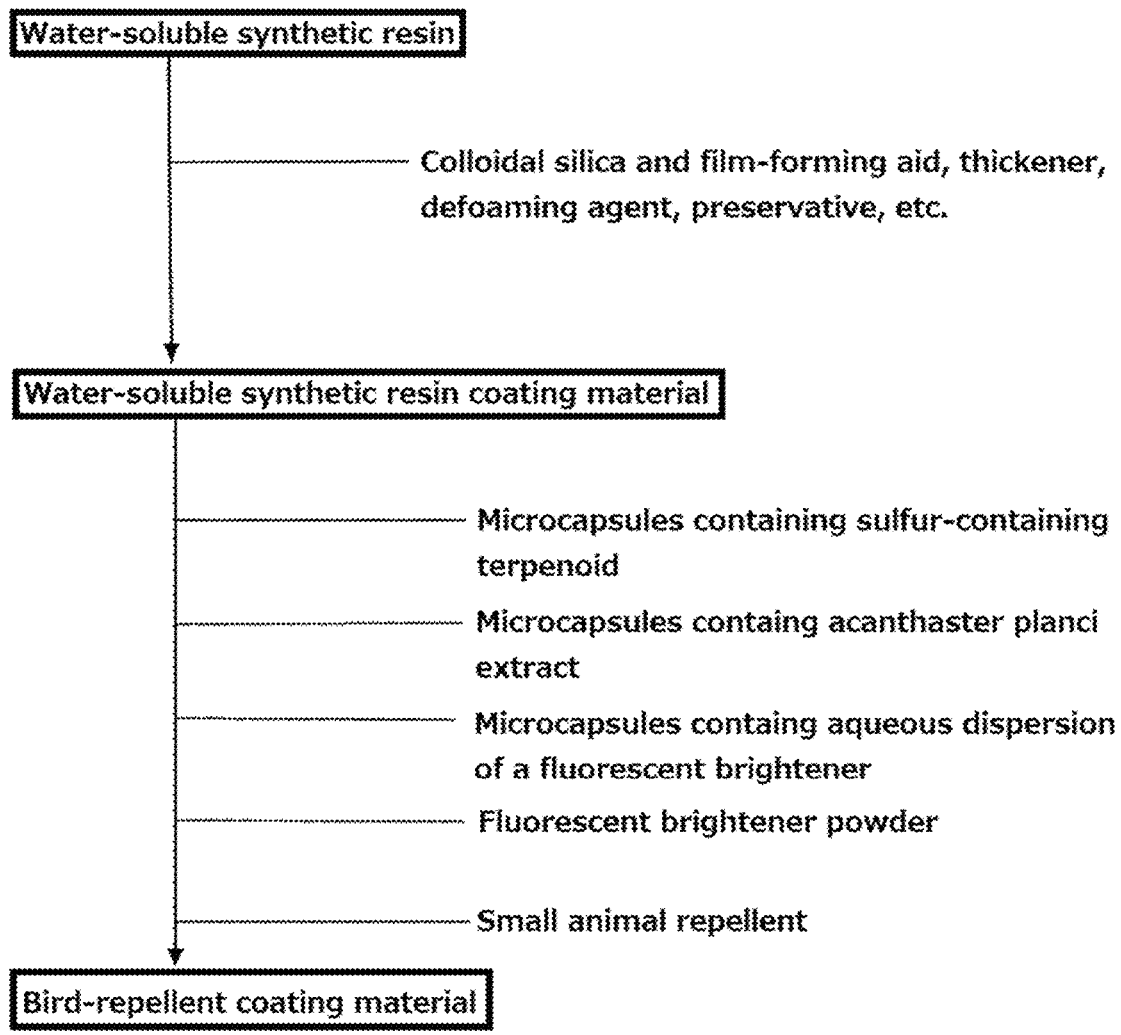
[Fig. 7]
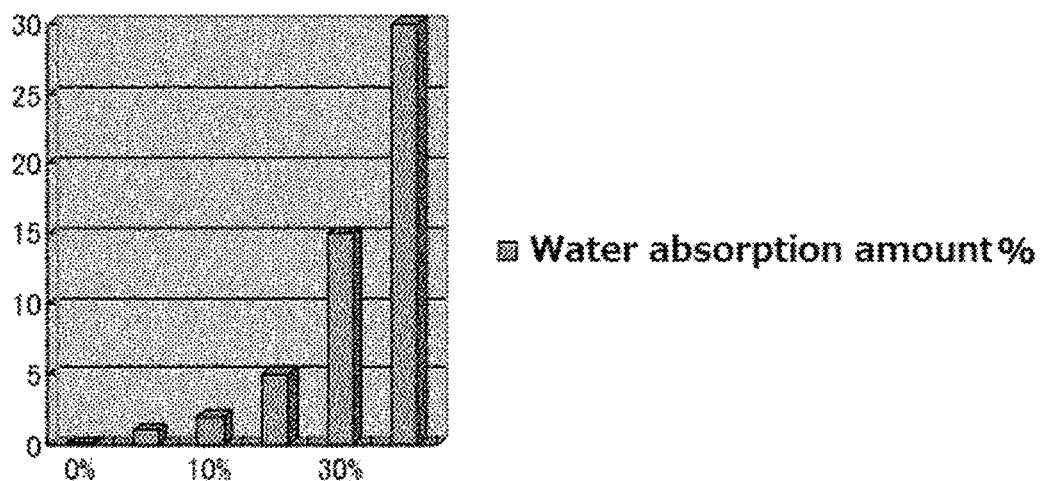

BIRD-REPELLENT COATING MATERIAL

TECHNICAL FIELD

The present invention relates to a bird-repellent coating material.

BACKGROUND ART

Damage caused by birds has been reported in not only everyday living areas but also all human-related environments such as factories, station buildings and airports. Urgent countermeasures against birds as viral transmission sources, in addition to as fecal pollution sources and the like, are recently required. Disasters caused by intrusion of birds into aircraft engines, so-called bird strikes in airports, are reported throughout the world, against which relevant corresponding countermeasures have been conventionally studied.

Examples of such measures include a wide variety of approaches such as devices, magnets, nets and coating materials. In the current situation, however, no adequate measure has been developed, for instance, in terms of cost, bird type, environmental issues (e.g., toxicity, odor and noise), installation location and durability of effects.

As bird repellents, for instance, Japanese Patent Application Publication No. 2002-173401 discloses a repellent of rhubafuran, and cinnamyl nitrile or vertacetal, and Japanese Patent Application Publication No. H09-301803 discloses sulfur-containing terpene compounds and sulfur-containing/oxygen-containing heterocyclic compounds. However, these repellents are volatile, and accordingly are problematic in that durability of effects of the repellent is poor for practical use.

CITATION LIST

Patent Literature

[PTL 1] Japanese Patent Application Publication No. 2002-173401
[PTL 2] Japanese Patent Application Publication No. H09-301803

SUMMARY OF INVENTION

Technical Problem

Methods for preventing bird damage from pigeons and crows by relying on coating materials are superior by virtue of not involving harm factors (1) to (3) below, and accordingly have been proposed conventionally. Prior art instances of repellent coating materials, for example repellents containing capsaicin and/or lanolic acid ester, are effective in cases where the birds ingest the coating film, but are ineffective in terms of preventing the coming of birds.

(1) Repellent measures relying on sound are not possible in some cases on account of the installation location.
(2) Nets, various types of thread, pins and the like are limited as regards installation location, and require frequent maintenance.
(3) Adhesive-based repellents contaminate the environment and deliver a short adhesive effect, and hence are transient repellents.

Solvent-based, fragrance-based, plasticizer-based, amine-based and fierce animal excreta-based coating materials are problematic in terms of durability of effects and environmental contamination due to those bad small and volatility. The approach of formulating other toxic repellents such as agrichemicals into a coating material has also been addressed, but such repellents are difficult to use when their impact on human society is considered.

It is an object of the present invention to provide a bird-repellent coating material that is excellent in application workability, is highly safe and environment-friendly, and affords a bird repellent effect that is sustained over long periods of time.

Solution to Problem

A bird-repellent coating material according to an aspect of the present invention is a bird-repellent coating material wherein at least one selected from the group consisting of a microencapsulated aqueous dispersion of a visual repellent against birds, a microencapsulated volatile olfactory repellent against birds and a powder of a visual repellent against birds is incorporated into an aqueous resin vehicle.

In the above bird-repellent coating material, preferably, the visual repellent against birds in the aqueous dispersion of a visual repellent against birds is at least one of an ultraviolet reflecting agent and an ultraviolet-absorbing fluorescent agent.

In the above bird-repellent coating material, preferably, the visual repellent against birds that constitutes the powder of the visual repellent against birds is at least one of an ultraviolet reflecting agent and an ultraviolet-absorbing fluorescent agent.

In the above bird-repellent coating material, preferably, the ultraviolet reflecting agent is cesium oxide.

In the above bird-repellent coating material, preferably, the ultraviolet-absorbing fluorescent agent is at least one selected from the group consisting of a fluorescent brightener, a fluorescent protein and a water extract of Acanthaster planci powder.

In the above bird-repellent coating material, preferably, the volatile olfactory repellent against birds is at least one selected from the group consisting of a sulfur-containing terpenoid, a sulfur-containing/oxygen-containing heterocyclic compound, rhubafuran (2,4-Dimethyl-4-phenyl tetrahydrofuran), cinnamyl nitrile (Trans-β-phenyl acrylonitrile) and vertacetal (Acetaldehyde 2-phenyl-2,4-pentandiol acetal).

In the above bird-repellent coating material, preferably, the proportion of the total mass of "at least one of the visual repellents against birds, which are the visual repellent against birds in the microencapsulated aqueous dispersion of a visual repellent against birds and the visual repellent against birds that constitutes the powder of the visual repellent against birds" and "the volatile olfactory repellent against birds", with respect to the "mass of a non-volatile fraction", is in the range of 0.1 mass % to 20 mass %.

In the above bird-repellent coating material, preferably, a small animal repellent that prevents intrusion of small animals is further incorporated into the aqueous resin vehicle as a measure against birds of prey that pursue small animals. In the description of the present application, the term small animal does not encompass birds. That is because although the repellent effect on the sense of smell and taste of birds of prey is weak, and thus no direct effect is elicited on these, the coming of birds of prey can nevertheless be prevented by forestalling the intrusion of small animals, which are pursued by birds of prey. In that case, preferably, the proportion of the total mass of "at least one of the visual repellents against birds, which are the visual repellent against birds in the microencapsulated aqueous dispersion of a visual repellent against birds and the visual repellent against birds that constitutes the powder of the visual repellent against birds", "the volatile olfactory repellent against birds" and "the small animal repellent", with respect to the "mass of a non-volatile fraction", is in the range of 0.1 mass % to 20 mass %.

In the above bird-repellent coating material, preferably, colloidal silica is further incorporated into the aqueous resin vehicle.

The present invention can also be expressed as: "a method of using, as a bird-repellent coating material, a product resulting from incorporating, into an aqueous resin vehicle, at least one selected from the group consisting of a microencapsulated aqueous dispersion of a visual repellent against birds, a microencapsulated volatile olfactory repellent against birds and a powder of a visual repellent against birds"; "at least one selected from the group consisting of a microencapsulated aqueous dispersion of a visual repellent against birds, a microencapsulated volatile olfactory repellent against birds and a powder of a visual repellent against birds, for use as a bird-repellent coating material"; and "a method for inhibiting or preventing the approach of birds to an object by coating the object, present in a space visited by the birds come, with a coating material obtained by incorporating, into an aqueous resin vehicle, at least one selected from the group consisting of a microencapsulated aqueous dispersion of a visual repellent against birds, a microencapsulated volatile olfactory repellent against birds and a powder of a visual repellent against birds". From another viewpoint, the present invention can also be expressed as "at least one selected from the group consisting of a microencapsulated aqueous dispersion of a visual repellent against birds, a microencapsulated volatile olfactory repellent against birds and a powder of a visual repellent against birds, for producing a coating material for repelling birds".

Advantageous Effects of Invention

In the present invention, a sustained effect as a bird-repellent coating material is achieved by filling microcapsules with an aqueous dispersion of a visual repellent against birds or volatile olfactory repellent against birds, and incorporating the microcapsules into an aqueous resin vehicle, or by alternatively incorporating a powder of a visual repellent against birds into an aqueous resin vehicle. The above effect can be further enhanced by incorporating colloidal silica into the resin vehicle. The present invention is a superior bird-repellent coating material in which the characteristics of various birds are factored in, for instance, susceptibility to olfactory stress in pigeons and to visual stress in crows. The bird-repellent coating material is an aqueous material and accordingly boasts excellent application workability, environmental friendliness and high safety. Therefore, the bird-repellent coating material can be used in various buildings such as condominiums and various sites such as station buildings. The bird-repellent coating material can yield an effective means as a bird, strike countermeasure in aircraft at airports. Further, the bird-repellent coating material is compatible with dedicated primers, when applied onto an underlying base of metal, asphalt, old paint or the like.

BRIEF DESCRIPTION OF DRAWINGS

FIG. 1 is a schematic diagram of a microcapsule having a fluorescent brightener aqueous dispersion encapsulated therein.

FIG. 2 is a schematic diagram of a microcapsule having a sulfur-containing terpenoid encapsulated therein.

FIG. 3 is a schematic diagram of a microcapsule having an Acanthaster planci water extract encapsulated therein.

FIG. 4 is a schematic diagram illustrating an example of a coating material composition.

FIG. 5 is a schematic diagram of an instance where a bird-repellent coating material of the present invention is applied onto a metallic part.

FIG. 6 is a flowchart illustrating a production process of a bird-repellent coating material.

FIG. 7 is a graph illustrating the results of a field test of repellent effect on crows, where the vertical axis represents water supply volume (%) and the horizontal axis represents total addition amount of visual repellent against birds plus volatile olfactory repellent against birds.

DESCRIPTION OF EMBODIMENTS

A bird-repellent coating material according to an embodiment of the present invention contains a visual repellent against birds and/or a volatile olfactory repellent against birds (the terms "visual repellent against birds" and "volatile olfactory repellent against birds" may hereafter be notated collectively as "bird repellent component"). Examples of the visual repellent against birds include ultraviolet reflecting agents and ultraviolet-absorbing fluorescent agents. Examples of ultraviolet reflecting agents include, for instance, cesium oxide. Examples of ultraviolet-absorbing fluorescent agents include, for instance, aqueous dispersions of fluorescent brighteners and fluorescent proteins, or water extracts of powdery fluorescent brighteners or fluorescent proteins, or of a dry powder of Acanthaster planci. Examples of the volatile olfactory repellent against birds include sulfur-containing terpenoids, sulfur-containing/oxygen-containing heterocyclic compounds, rhubafuran, cinnamyl nitrile and vertacetal. Among the foregoing, liquid bird repellent components in the form, for instance, of a liquid, an aqueous dispersion or a water extract are used in a state where the bird repellent component is encapsulated in microcapsules. Microencapsulation is carried out prior to production of the coating material. The particle size of the microcapsules is preferably in the range of 1 μm to 100 μm, for instance, from the viewpoint of finishing and workability of the coating material.

A coating material containing at least one of a microencapsulated volatile olfactory repellent against birds, microcapsules filled with a water-dispersed visual repellent against birds, and a powder of a visual repellent against birds which are incorporated into an aqueous resin vehicle is prepared, and the prepared coating material is applied onto the required site.

The volatile olfactory repellent against birds in an embodiment of the present invention is, for instance, a sulfur-containing terpenoid, a sulfur-containing/oxygen-containing heterocyclic compound, rhubafuran, cinnamyl nitrile or vertacetal. In order to sustain the effect of foregoing over long periods of time, these volatile olfactory repellent against birds are encapsulated in microcapsules to thereby be released in a sustained manner.

The term ultraviolet-absorbing fluorescent agent in an embodiment of the present invention denotes a substance that emits fluorescent light derived from ultraviolet rays. Examples of the ultraviolet-absorbing fluorescent agent include, for instance, fluorescent brighteners such as the compounds represented by the chemical formulas below, as well as fluorescent proteins and a water extract of Acanthaster planci powder. In the embodiments of the present invention, the term ultraviolet reflecting agent denotes a substance that reflects ultraviolet rays. Examples of ultraviolet reflecting agents include, for instance, cesium oxide. The ultraviolet reflecting agent can be used by being dispersed in water and being encapsulated into microcapsules, or can be used in powder form.

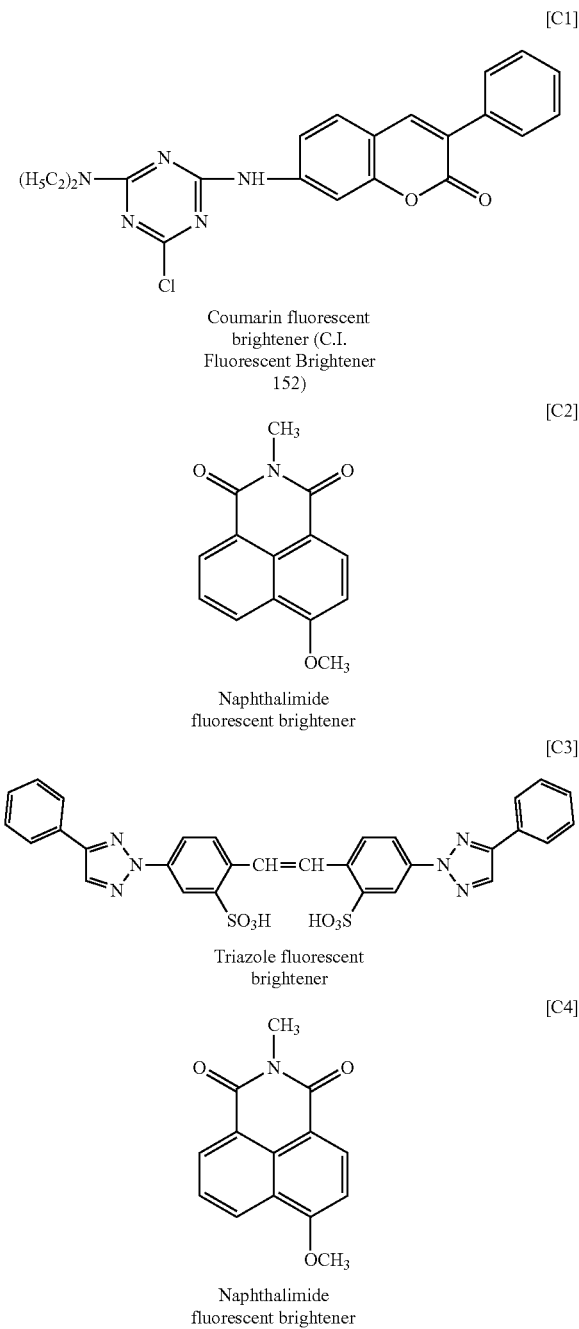

[C1] Coumarin fluorescent brightener (C.I. Fluorescent Brightener 152)

[C2] Naphthalimide fluorescent brightener

[C3] Triazole fluorescent brightener

[C4] Naphthalimide fluorescent brightener

In addition to at least one of a visual repellent against birds and a volatile olfactory repellent against birds such as the above, preferably the bird-repellent, coating material according to an embodiment of the present invention further contains a small animal repellent which prevents intrusion of small animals, as a countermeasure against birds/beasts that prey on small animals (excluding birds). Examples of small animal repellents that prevent the intrusion of small animals, which as the diet of birds of prey are one cause of the appearance of such birds, include the following: menthol, limonene, linalool, mitral, diethyl triamide, capsaicin, stemone, dihydrobenzole, 2-isopropyl-5 methylphenol, peppermint natural oil, geranium oil, eucalyptus oil, hiba (Thujopsis) oil, garlic oil and bamboo vinegar.

The addition ratio of the bird repellent component in the bird-repellent coating material is established taking into consideration the bird repellent effect of the component and the performance thereof as a coating material, for instance, in terms of adhesion and durability. Specifically, the proportion of the total of the visual repellent against birds and the volatile olfactory repellent against birds, or of the total of the visual repellent against birds, the volatile olfactory repellent against birds and the small animal repellent, is preferably in the range of 0.1 mass % to 20 mass %, with respect to 100% as the non-volatile fraction of the bird-repellent coating material.

As the microcapsules filled with an aqueous dispersion of a visual repellent against birds or a volatile olfactory repellent against birds according to an embodiment of the present invention there are preferably used microcapsules that encapsulate and stabilize the aqueous dispersion of a visual repellent against birds or the volatile olfactory repellent against birds, being liquids, and that make volatilization of the volatile olfactory repellent against birds into sustained release. In the bird-repellent coating material according to an embodiment of the present invention, preferably, colloidal silica, which imparts air permeability to coating films and facilitates volatilization of the volatile olfactory repellent against birds, is incorporated into an aqueous resin vehicle.

Preferably, the aqueous dispersion of a visual repellent against birds or the volatile olfactory repellent against birds is encapsulated into microcapsules prior to the production of the coating material. Examples of encapsulation methods include, for instance, a method that involves dispersing microcapsules and an aqueous dispersion of a visual repellent against birds or volatile olfactory repellent against birds using a stirrer, leaving the resulting dispersion to stand for one day, and thereafter filtering the dispersion to retrieve the microcapsules having the aqueous dispersion of a visual repellent against birds or volatile olfactory repellent against birds encapsulated therein. The forming component of the microcapsules may be synthetic resin-based, for instance, a silicone resin or a urethane resin, or may be inorganic-based, for instance, glass or a ceramic. The diameter of the microcapsules that can be used in the bird-repellent coating material is preferably in the range of 0.1 μm to 100 μm.

Examples of resin vehicles include, for instance, aqueous emulsions and water-soluble resin vehicles. Examples of resins include, for instance, acrylic resins, silicone resins, urethane resins and fluororesins. Preferably, all the foregoing resins are a synthetic resin having excellent outdoor weatherability and adhesion.

The bird-repellent coating material may contain various additives as needed, for instance, defoaming agents, film-forming aids, viscosity adjusting agents and pH adjusting agents. Preferably no pigments are used, since these would impair the effect of the visual repellent against birds. Preferably, colloidal silica is incorporated in order to elicit moderate volatilization of the volatile olfactory repellent against birds from within the coating film. Colloidal silica is a preferred material in the present invention as an additive for imparting air permeability to the coating film.

The proportion of the total of the visual repellent against birds and the volatile olfactory repellent against birds, or the total of the visual repellent against birds, the volatile olfactory repellent against birds and the small animal repellent, with respect to the non-volatile fraction of the bird-repellent coating material, is preferably set to be in the range of 0.1 mass % to 20 mass %. If the above proportion is too low, the bird repellent effect is weak, whereas if the proportion is too high, problems may arise as regards the physical properties of the coating film, for instance, in terms of water resistance, workability and weatherability. The above range is preferably narrowed down to 8 mass % to 10 mass %.

FIG. 7 illustrates the influence of the addition amount of the visual repellent against birds and volatile olfactory repellent against birds on the water absorption ratio of the bird-repellent coating film. The water absorption amount is best small, and ordinarily is preferably 2 mass % or less.

The bird-repellent coating material is applied to sites where damage is caused by intrusion of birds. In order to sustain the bird repellent effect over long periods of time it is essential that the coating material should match the performance of ordinary coating materials. Factors to be considered include the underlying base of the coating material and the weather during application. Sites where the bird-repellent coating material is applied include, for instance, habitable construction structures such as condominiums, civil engineering structures such as airports, and public buildings such as stations. The coating underlying base may be of metal, concrete, asphalt, aluminum, wood or the like. Primers and coating system that are suitable for the bird-repellent coating material have been established. The bird repellent effect can be sustained over long periods of time by virtue of the coating method and the bird-repellent coating material.

EXAMPLES

A coating material was produced by adding microcapsules filled with a volatile olfactory repellent against birds, adding at least one of an ultraviolet reflecting agent and an ultraviolet-absorbing fluorescent agent, for birds having the trait of shunning luminous bodies, and adding a small animal repellent, exploiting the indirect effect of such a repellent as a solution to intrusion of birds of prey. Highly safe natural components or components already publicly used were utilized herein in all the bird repellent components. Colloidal silica, which allows imparting air permeability to coating films, was added so as to enable the volatile olfactory repellent against birds to volatilize stably from the coating film.

The bird-repellent coating material according to an embodiment of the present invention is a coating material, boasting excellent repellency, in which the characteristics of various birds are factored in, for instance, susceptibility to olfactory stress in pigeons and to visual stress in crows. The bird-repellent coating material is an aqueous material. Accordingly, the coating material affords excellent application workability and is environmentally friendly, and highly safe. The coating material was targeted for use also in buildings such as condominiums and at various locations such as station buildings, where opportunities for contact with humans arise. The coating material is further an effective means as a countermeasure against aircraft-striking birds in airports. By virtue of being in paint form, the coating material is compatible with any underlying base. For instance, the coating material is compatible with dedicated undercoat materials such as metal, asphalt, or old paint.

The microencapsulation method of the aqueous dispersion of a visual repellent against birds and the volatile olfactory repellent against birds is as given in (1) and (2) below.

(1)

(1-1)

In a case where a water extract of Acanthaster planci powder is used as the bird repellent component, firstly an Acanthaster planci powder is added to water to a content of Acanthaster planci powder in the range of 1 mass % to 50 mass %, and thereafter a preservative is added to the water. The Acanthaster planci powder-containing water is then stirred for 1 to 2 hours at 100 to 2000 RPM, after which the resulting Acanthaster planci powder-containing water is allowed to stand overnight. Thereafter, the Acanthaster planci powder-containing water is stirred again, the Acanthaster planci powder is filtered from the Acanthaster planci powder-containing water, and the filtrate is dried, to yield a water extract of Acanthaster planci powder.

(1-2)

In a case where a fluorescent brightener is used as the bird repellent component, the fluorescent brightener is added to water so that the content of the fluorescent brightener may be in the range of 1 mass % to 50 mass %, after which the fluorescent brightener-containing water is stirred at 100 to 2000 RPM, to thereby disperse of the fluorescent brightener in the water.

(1-3)

Sulfur-containing terpenoids are liquid and hence are used directly.

(2) The bird repellent component and microcapsules are mixed so that the ratio of bird repellent component/microcapsules may be in the range of 1/1 to 3/1, and the resulting mixture is stirred at low speed (about 100 RPM). Thereafter, the mixture is allowed to stand overnight, and is filtered, to separate the microcapsules having the bird repellent component encapsulated therein.

By way of example, field tests (Table 1) were conducted in which a single volatile olfactory repellent against birds and a single visual repellent against birds, or one volatile olfactory repellent against birds and one or two visual repellents against birds, were incorporated into a respective coating material. Good coating materials among the foregoing were tested in actual locations, and the effect of the materials was assessed.

TABLE 1

|  | Examples | | | | | | | Comparative |
|---|---|---|---|---|---|---|---|---|
|  | 1 | 2 | 3 | 4 | 5 | 6 | 7 | example |
| Silicone emulsion | 50 | 50 | 50 | 50 | 50 | 50 | 50 | 50 |
| Colloidal silica | 10 | 10 | 10 | 10 | 10 | 10 | 10 | 10 |

TABLE 1-continued

| | Examples | | | | | | | Comparative example |
|---|---|---|---|---|---|---|---|---|
| | 1 | 2 | 3 | 4 | 5 | 6 | 7 | |
| Film-forming aid | 5 | 5 | 5 | 5 | 5 | 5 | 5 | 5 |
| Defoaming agent | 0.5 | 0.5 | 0.5 | 0.5 | 0.5 | 0.5 | 0.5 | 0.5 |
| Thickener | 2.5 | 2.5 | 2.5 | 2.5 | 2.5 | 2.5 | 2.5 | 2.5 |
| Preservative | 0.1 | 0.1 | 0.1 | 0.1 | 0.1 | 0.1 | 0.1 | 0.1 |
| Water | 26.9 | 26.9 | 26.9 | 28.9 | 22.9 | 25.9 | 25.9 | 31.9 |
| A sulfur-containing terpenoid capsules | 5 | | | | 3 | 3 | 3 | |
| B1 Acanthaster planci capsules | | 5 | | | 3 | | | |
| B2 fluorescent brightener capsules | | | 5 | | 3 | 3 | | |
| B3 fluorescent brightener powder | | | | 3 | | | 3 | |
| Total (wt %) | 100 | 100 | 100 | 100 | 100 | 100 | 100 | 100 |

A: volatile olfactory repellent against birds;
B1 to B3: visual repellent against birds <Field Test on Repellent Effect Against Pigeons>

The bird repellent effect of the bird-repellent coating materials in an example was evaluated in a shrine of Osaka. For evaluation there were prepared two specimens each of 30 cm plywood boards coated with respective bird-repellent coating materials of Examples 1 to 6 (coating amount: 150 g/m$^2$; two coats), followed by drying. The total of 12 plywood boards coated with the bird-repellent coating materials were randomly set in a park, raw grains and edible peanuts were sprinkled on the coated surface of the plywood boards coated with the bird-repellent coating materials, and the eating behavior of pigeons was observed. Observations were carried out thrice in different days (modifying each time the installation location of the plywood boards coated with the bird-repellent coating materials). The repellent effect on pigeons was evaluated comprehensively taking into account the three observations. The evaluation of the repellent effect was as given in Table 2. The reference symbols A to D in the results of Table 2 denote the events in brackets below.
A: highly effective (no pigeons settle)
B: effective (some pigeons settle but do not eat)
C: somewhat effective (some pigeons settle and eat)
D: ineffective (pigeons settle and eat everything)

TABLE 2

<Test results>

| Test | | Result |
|---|---|---|
| Example | 1 | A to B |
| | 2 | C |
| | 3 | C |
| | 4 | C |
| | 5 | B |
| | 6 | B |
| | 7 | B |
| Comparative example | | D |

<Field Test on Repellent Effect Against Crows>

The bird repellent effect of the bird-repellent coating materials in the examples was evaluated in a selected park of Osaka, as an area where domestic garbage is discarded. The evaluation of the repellent effect was as given in Table 3.

TABLE 3

<Test results>

| Test | | Result |
|---|---|---|
| Example | 1 | C |
| | 2 | B |
| | 3 | B |
| | 4 | B |
| | 5 | B to A |
| | 6 | B to A |
| | 7 | B to A |
| Comparative example | | D |

<Field Application Example: Railway Station Building in Osaka>

The bird-repellent coating material of Example 1 was applied at ceiling metallic parts of the station, where pigeons had been reported to perch and generate fecal pollution for passengers standing on the platforms. Reports from the railway administration indicated that the effect against pigeons was dramatic. Later on the railway reported that the same bird-repellent coating material had been adopted against pigeon pollution in multiple stations.

<Field Application Example: Planned Town in Nara Prefecture>

An experiment was carried out at an area of confirmed damage by garbage-scavenging crows on twice-weekly domestic garbage collection days. Specifically, an experiment was carried out by using a polyester net against birds (product name: Bird stopper net, 25 mm mesh, yellow) coated beforehand with the coating materials of Examples 5 and 7. Raw garbage bags covered with an uncoated net, those covered with a coated net, and those without any nets were compared. The evaluation of the repellent effect was as given in Table 4.

TABLE 4

| Test | Result |
| --- | --- |
| No net | Birds come, tear the bag and scavenge the contents |
| Only net | Birds come but give up on tearing the bag |
| Coated net (Example 5) | No birds come |
| Coated net (Example 7) | No birds come |

<Addition Amount of the Bird Repellent Component in the Bird-Repellent Coating Material>

Both a. sulfur-containing terpenes and b. Acanthaster planci extracts, being bird repellent components, are liquid and hence it is deemed that they exhibit a plasticizer-like behavior in the bird-repellent coating material; Moreover, these bird repellent components are expensive substances. Accordingly, the addition amount of the bird repellent components in the bird-repellent coating material was assessed both from the performance aspect and the economic aspect.

Each bird repellent component was mixed with an aqueous silicone coating material having 40% solids, to a content of 0, 3, 5, 10 and 20 mass % of the bird repellent component, and water resistance was assessed. The bird repellent components that were used were not microencapsulated, i.e. the components were used as they were. Firstly, a specimen was prepared by applying a respective bird-repellent coating material on a glass plate with a 10-mil applicator, with drying for 7 days. Thereafter, the specimen was immersed for 5 hours in water, was retrieved, and the coating film was then observed. The results were as given in Table 5.

TABLE 5

| Amount (%) | | Coating film state | Evaluation |
| --- | --- | --- | --- |
| A | B | | |
| 0 | 0 | No abnormality | A |
| 3 | | Whitening but reverting to normal | B |
| | 3 | Whitening but reverting to normal | B |
| 5 | | Whitening but reverting to normal | B |
| | 5 | Whitening but reverting to normal | B |
| 10 | | Whitening/blistering | D |
| | 10 | Whitening/blistering | D |
| 20 | | Whitening/peeling | D |
| | 20 | Whitening/peeling | D |

<Effect of Microcapsules>

The effect of encapsulating the bird repellent component into microcapsules was checked. a: a respective coating material was added to encapsulation microcapsules (prepared prior to the test, with 5 parts by mass of bird repellent component with respect to 3 parts by mass of microcapsules). b: 5 parts of bird repellent component were directly added to the coating material. The coating material comprising the bird repellent component was applied, at 150 g/m², onto a slate board having painted beforehand with an undercoat, and then the coating was dried for 7 days. Thereafter, the slate board with the coating film was exposed in an accelerated weathering tester, Sunshine Weatherometer for 300 hours (outdoor exposure of about 1 year), and the effect of the microcapsules was assessed. The particle size of the microcapsules was 100µ.

<Olfactory Sensory Test of Sulfur-Containing Terpenoids>

Table 6 summarizes the results of an olfactory sensory test by five people.

TABLE 6

| | Before test | After exposure |
| --- | --- | --- |
| a | A: strong odor | B: good odor |
| b | A: strong odor | C to D: faint odor |

In the case of direct addition of the repellent, it is found that b exhibits a greater drop in repellent effect, caused by adsorption and reaction of the component in the coating material, and greater volatilization of the component by moisture and heat upon exposure, as compared with the case of a, where the component is protected in the microcapsules.

<Intensity of Reflected Light of the Acanthaster Planci Solution>

The intensity of reflected light from black light, elicited by respective Acanthaster planci solutions, was as given in Table 7.

TABLE 7

| | Before test | After exposure |
| --- | --- | --- |
| a | A: good gleam | B: gleam but fainter than before test |
| b | B: gleam but fainter than a | C to D: faint gleam |

It is deemed that in the case (b), where bird repellent component is directly added to the coating material, there is a greater drop in effect, caused by adsorption and reaction of the bird repellent component in the coating material, and greater volatilization of the component by moisture and heat upon exposure, as compared with the case of (a), where the component is protected in the microcapsules.

INDUSTRIAL APPLICABILITY

The bird-repellent coating material according to the present invention, being a coating material that prevents damage by birds, in particular pigeons and crows, can be easily applied and installed, by virtue of its properties as a paint, regardless of the shape and material of the underlying foundation, and encompasses thus a broad scope of industrial uses. As regards pigeons, for instance, examples of the use of the coating material include limitation of damage to passengers caused by fecal pollution in station buildings, prevention of fecal pollution in industrial products, and damage prevention in shrine and temple buildings. In the case of crows, uses of the coating material include, for instance, prevention of damage caused by scattering of domestic garbage, prevention of bird strikes in aircraft, and noise prevention.

REFERENCE SIGNS LIST

EH Acanthaster planci extract
FD Aqueous dispersion of fluorescent brightener
FL Bird-repellent coating material
FP Metallic part
MC Microcapsule
ME Microcapsule containing an Acanthaster planci extract
MF Microcapsule containing a fluorescent brightener aqueous dispersion
MS Microcapsule containing a sulfur-containing terpenoid
PR Primer
PW Fluorescent brightener powder
SA Small animal repellent
ST Sulfur-containing terpenoid
WR Water-soluble synthetic resin

The invention claimed is:

1. A bird-repellent coating material comprising:
    a microencapsulated aqueous dispersion of a visual repellent against birds; and
    an aqueous resin vehicle,
    wherein the microencapsulated aqueous dispersion of the visual repellent against birds is incorporated into the aqueous resin vehicle.

2. The bird-repellent coating material of claim 1,
    wherein the visual repellent against birds in the aqueous dispersion of the visual repellent against birds is at least one selected from the group consisting of a fluorescent brightener, a fluorescent protein, and a water extract of Acanthaster planci powder.

3. The bird-repellent coating material of claim 1, further comprising:
    a microencapsulated volatile olfactory repellent against birds,
    wherein the microencapsulated volatile olfactory repellent against birds is incorporated into the aqueous resin vehicle.

4. The bird-repellent coating material of claim 3,
    wherein the volatile olfactory repellent against birds is at least one selected from the group consisting of a sulfur-containing terpenoid, a sulfur-containing heterocyclic compound, an oxygen-containing heterocyclic compound, rhubafuran, cinnamyl nitrile, and vertacetal.

5. The bird-repellent coating material of claim 1, further comprising:
    a powder of a visual repellent against birds,
    wherein the powder of the visual repellent against birds is incorporated into the aqueous resin vehicle.

6. The bird-repellent coating material of claim 1, further comprising:
    at least one selected from the group consisting of a microencapsulated volatile olfactory repellent against birds and a powder of a visual repellent against birds incorporated into the aqueous resin vehicle,
    wherein a mass of repellents against birds with respect to a mass of a non-volatile fraction is in a range of 0.1 mass % to 20 mass %,
    wherein the mass of repellents against birds include a mass of the visual repellent against birds in the aqueous dispersion of the visual repellent against birds, and one or more of:
        a mass of the volatile olfactory repellent against birds, and
        a mass of the visual repellent against birds that constitutes the powder of the visual repellent against birds.

7. The bird-repellent coating material of claim 1, further comprising:
    a small animal repellent that prevents intrusion of small animals excluding birds,
    wherein the small animal repellent is incorporated into the aqueous resin vehicle.

8. The bird-repellent coating material of claim 7, further comprising:
    at least one selected from the group consisting of a microencapsulated volatile olfactory repellent against birds and a powder of a visual repellent against birds incorporated into the aqueous resin vehicle,
    wherein a mass of repellents with respect to a mass of a non-volatile fraction is in a range of 0.1 mass % to 20 mass %,
    wherein the mass of repellents include a mass of the visual repellent against birds in the aqueous dispersion of the visual repellent against birds, a mass of the small animal repellent, and one or more of:
        a mass of the volatile olfactory repellent against birds, and
        a mass of the visual repellent against birds that constitutes the powder of the visual repellent against birds.

9. The bird-repellent coating material of claim 1, further comprising:
    a colloidal silica,
    wherein the colloidal silica is incorporated into the aqueous resin vehicle.

* * * * *